(12) United States Patent
Darmstadt et al.

(10) Patent No.: US 9,176,154 B2
(45) Date of Patent: Nov. 3, 2015

(54) CALIBRATION PROCESS AND SYSTEM

(71) Applicant: Bio-Rad Laboratories, Inc., Hercules, CA (US)

(72) Inventors: Adam Darmstadt, Hercules, CA (US); Michael Waite, Hercules, CA (US); Theresa Forni, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 14/100,397

(22) Filed: Dec. 9, 2013

(65) Prior Publication Data

US 2014/0157859 A1    Jun. 12, 2014

Related U.S. Application Data

(60) Provisional application No. 61/736,389, filed on Dec. 12, 2012.

(51) Int. Cl.
*G01D 18/00* (2006.01)
*G01N 35/00* (2006.01)

(52) U.S. Cl.
CPC ............ *G01N 35/00693* (2013.01); *G01N 2035/00702* (2013.01)

(58) Field of Classification Search
CPC ............ A61B 5/14532; A61B 5/1495; G01N 27/4163; G01N 2001/2893; G01N 35/1002; G01N 35/00594; G01N 35/00693; G01N 21/274; G01N 33/0006; G01N 35/00732
USPC ........................................ 73/1.02, 1.03, 61.52
See application file for complete search history.

(56) References Cited

U.S. PATENT DOCUMENTS

| | | | |
|---|---|---|---|
| 3,874,850 A | 4/1975 | Sorensen et al. | |
| 3,885,414 A | 5/1975 | Reville | |
| 5,229,074 A | 7/1993 | Heath et al. | |
| 6,684,680 B2 | 2/2004 | Pierskalla et al. | |
| 2003/0097229 A1 | 5/2003 | Herrmann et al. | |
| 2005/0249634 A1* | 11/2005 | Devlin, Sr. | 422/64 |
| 2008/0102525 A1 | 5/2008 | Rannikko et al. | |
| 2009/0127454 A1 | 5/2009 | Ritchie et al. | |
| 2009/0301166 A1* | 12/2009 | Charlton et al. | 73/1.02 |
| 2010/0081579 A1 | 4/2010 | Bushway et al. | |
| 2010/0196945 A1* | 8/2010 | Forsell | 435/29 |

(Continued)

OTHER PUBLICATIONS

Author Unknown, "DCA Vantage TM Analyzer Operator's Guide", Seimens, REF 06489264 Rev. B, Jun. 2008, 164 pgs.

(Continued)

*Primary Examiner* — Eric S McCall
*Assistant Examiner* — Anthony W Megna Fuentes
(74) *Attorney, Agent, or Firm* — Kilpatrick Townsend & Stockton LLP

(57) ABSTRACT

An improved calibration process for a medical testing machine. The machine automatically recognizes that a package of calibration material has been inserted into it, and performs a calibration sequence to ascertain a calibration parameter to be used in performing future tests with the medical testing machine. The calibration package may include machine-readable indicators that the package is to be used for calibration, and of a calibration setpoint of a calibration material in the package. A calibration material may be stored in a lyophilized state in the package, and the medical testing machine may automatically reconstitute the lyophilized material.

17 Claims, 6 Drawing Sheets

(56) References Cited

U.S. PATENT DOCUMENTS

| | | | |
|---|---|---|---|
| 2010/0291691 A1* | 11/2010 | Sugiyama et al. | 436/67 |
| 2011/0184268 A1 | 7/2011 | Taub | |
| 2011/0303671 A1 | 12/2011 | Lowry | |
| 2012/0046203 A1 | 2/2012 | Walsh et al. | |
| 2012/0178091 A1 | 7/2012 | Glezer et al. | |
| 2012/0234393 A1 | 9/2012 | Maltezos | |
| 2012/0245447 A1 | 9/2012 | Karan et al. | |
| 2013/0132897 A1 | 5/2013 | Schultz et al. | |

OTHER PUBLICATIONS

International Search Report and Written Opinion of PCT/US/2013/074073, mailed on Jun. 6, 2014, 19 pages.

* cited by examiner

500

| Assay: | HbA1c ▼ |
|---|---|
| Lot Number: | AA82114 |
| Expiration: | 1/31/2013 ▼ |

| Component: | Assigned Value | | Stat Position |
|---|---|---|---|
| Conditioner | N/A | | 1 |
| Level 1 | 31.1 | mmol/mol | 2 |
| Level 2 | 93.4 | mmol/mol | 3 |

☐ Calibrate without reconstituting
(or calibrate with prediluted material)

| Open Stat Drawer | Calibrate Now | Cancel |

FIG. 5

CALIBRATION PROCESS AND SYSTEM

CROSS-REFERENCE TO RELATED APPLICATIONS

This application claims priority to U.S. Provisional Application No. 61/736,389 filed Dec. 12, 2012, entitled "Calibration Process and System," the entire disclosure of which is hereby incorporated by reference for all purposes as if fully set forth herein.

BACKGROUND OF THE INVENTION

In the diagnosis and monitoring of diseases, medical tests are often performed on blood, tissue, or other media sampled from patients. Such tests are often performed on automated testing machines. In a typical scenario, a doctor requests that a particular test be performed, and a sample is taken from the patient. The sample is sent to an on-site or off-site testing lab, and the results of the test are returned to the doctor for review and reporting to the patient.

In order to ensure proper diagnosis and treatment, a medical testing machine should be calibrated before its first use and periodically thereafter.

BRIEF SUMMARY OF THE INVENTION

According to one aspect, a method of performing a calibration in a medical testing machine includes automatically detecting that a package of calibration material has been inserted into the medical testing machine, and performing, by the medical testing machine, a calibration sequence using the calibration material to ascertain a calibration parameter for the medical testing machine. The method further includes storing the calibration parameter in electronic storage for use in later tests performed by the medical testing machine. In some embodiments, the method further includes reading a calibration setpoint from the package of calibration material. In some embodiments, the calibration material is provided in a lyophilized state, and the method further includes controlling the medical testing machine to automatically reconstitute the lyophilized material before performing the calibration sequence. In some embodiments, the medical testing machine performs liquid chromatography that uses a washing solution, and the washing solution is also used to reconstitute the lyophilized material. The method may further include agitating the reconstituted material by aspirating at least some of the reconstituted material from its vial and re-injecting the aspirated reconstituted material into its vial. The medical testing machine may perform high performance liquid chromatography. The medical testing machine may perform a test that measures a level of HbAlc hemoglobin in blood. In some embodiments, the method further comprises comparing the calibration parameter with a predetermined condition, and automatically re-running the calibration if the calibration parameter does not meet the predetermined condition. In some embodiments, the method further comprises comparing the calibration parameter with a predetermined condition, and automatically re-running the calibration if the calibration parameter meets the predetermined condition. The calibration may be a two-point calibration, in which two calibration parameters are ascertained. The calibration parameters may include a slope and an intercept.

According to another aspect, a medical testing machine comprises a testing system for performing a medical test on media sampled from patients, a media handling mechanism, a processor, and a memory. The memory holds instructions that when executed by the processor cause the medical testing machine to automatically recognize that a package of calibration material has been inserted into the medical testing machine, perform a calibration sequence using the calibration material to ascertain a calibration parameter for the medical testing machine, and store the calibration parameter in the memory for use in later tests performed by the medical testing machine. In some embodiments, the medical testing machine further includes a STAT input, and the medical testing machine automatically recognizes that the package of calibration material has been inserted into the STAT input. The medical testing machine may perform high performance liquid chromatography. The medical testing machine may perform a test that measures a level of HbAlc hemoglobin in blood. In some embodiments, the medical testing machine further includes a display, and the instructions, when executed by the processor, further cause the medical testing machine to present a user interface screen on the display indicating the progress of the calibration sequence. The display may be a touchscreen display.

According to another aspect, a package of calibration material for calibrating a medical testing machine comprises two materials, at least one of which is a calibration material, and a respective container for each of the materials. The containers maintain separation between the materials before use of the calibration package, and the containers are connected. In some embodiments one of the materials is a conditioning fluid. One of the materials may be a calibration material in a lyophilized state. In some embodiments, the package of calibration material includes two calibration materials and a conditioning fluid, each in respective containers. In some embodiments, the package of calibration material further includes a machine-readable indicator on the outside of the package that the package is for calibration of the medical testing machine. The machine-readable indicator may be a barcode. In some embodiments, the package of calibration material further includes a machine-readable indicator on the outside of the package of a calibration setpoint for one of the materials. The machine-readable indicator may be a barcode. In some embodiments, the package of calibration materials is in the shape of blood collection vials connected together.

BRIEF DESCRIPTION OF THE DRAWINGS

FIG. 5 illustrates an example user interface screen.

DETAILED DESCRIPTION OF THE INVENTION

Embodiments of the invention provide an improved calibration process for a medical testing machine.

One example of a condition that requires ongoing monitoring and repeated testing is diabetes. Diabetes is a name given to a class of conditions in which a patient exhibits elevated blood sugar levels, either because the patient's body does not produce enough of the metabolism-regulating hormone insulin, or because cells in the patient's body do not respond properly to insulin. Diabetes is increasingly prevalent in the United States and other parts of the world.

The management of diabetes often involves frequent blood sugar measurements, and many patients use at-home blood sugar testing devices to take frequent instantaneous readings of their blood sugar levels.

The patient's average blood glucose level over long periods of time, typically several months, is also reflected in the level of HbAlc hemoglobin in the patient's blood. Testing for HbAlc levels is more complex than testing for an instantaneous blood sugar level, and can be done using high performance liquid chromatography (HPLC) in a specialized testing machine. A patient may be tested several times per year and the resulting measured levels of HbAlc used as a check on how well the patient's blood sugar levels are being controlled.

Figure 1:
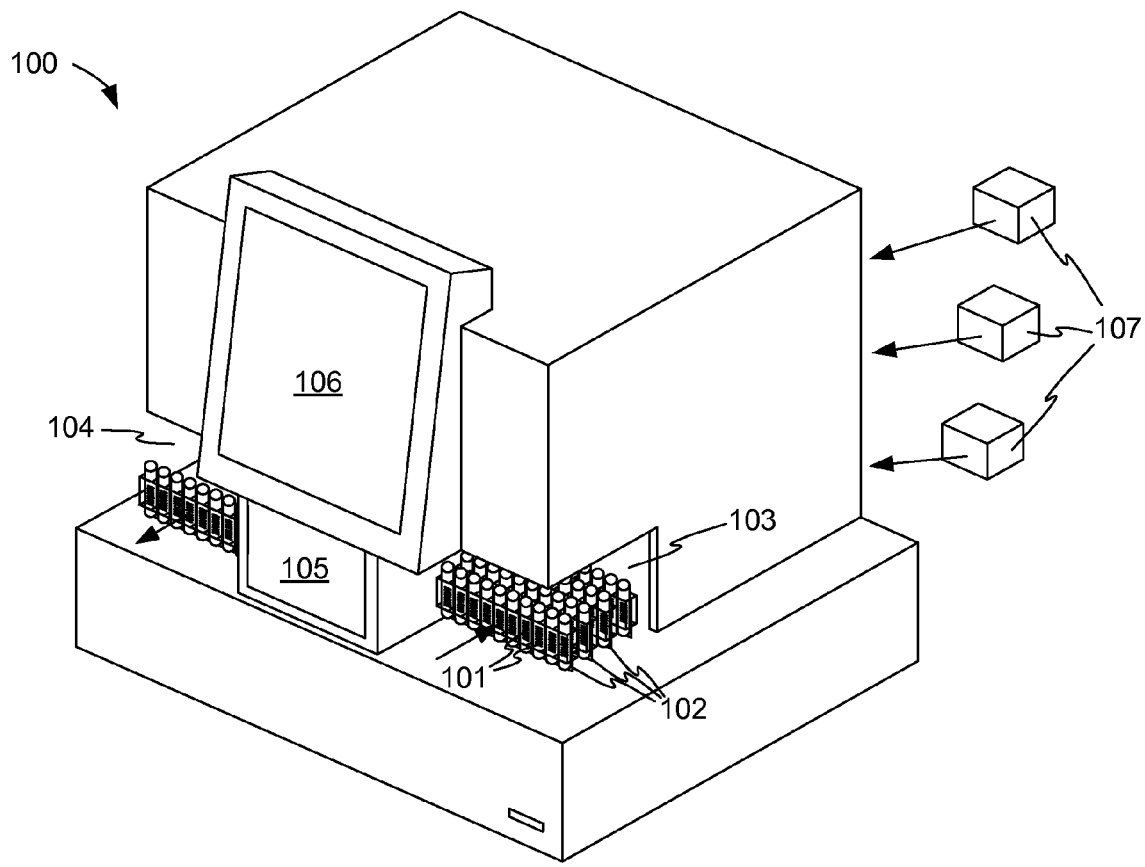
FIG. 1 shows a medical testing machine in accordance with example embodiments of the invention.

FIG. 1 shows a medical testing machine 100 in accordance with example embodiments of the invention. Example testing machine 100 is configured for testing blood samples for the level of HbAlc hemoglobin, but it will be understood that the principles of the invention are applicable to testing machines used for other purposes or with other technologies as well. Vials 101 containing blood sampled from patients are loaded into racks 102, which are then placed into testing machine 100 at input location 103. Vials 101 are examples of containers for patient media, but in other kinds of tests, other kinds of containers may be used. An automated testing system within medical testing machine 100 extracts a quantity from each vial in sequence, and for each sample performs HPLC to determine the level of HbAlc in the blood. When all of the vials in a rack have been tested, the rack is delivered out of the machine at output location 104. A "STAT input" 105 may be provided for initiating an out-of-sequence test. Placing a vial in STAT input 105 causes the vial to be tested with priority over the vials previously placed at input location 103.

Test results and other information are shown on a display screen 106. Display screen 106 may be any suitable type of display, for example a flat panel liquid crystal display (LCD). Display screen 106 may also include a touchscreen, and serve as an input device for receiving inputs from the user of medical testing machine 100.

HPLC by its nature uses certain consumable materials, for example buffers and washing solution, and packets 107 of consumable materials may be periodically replaced in medical testing machine 100. The stationary media used in HPLC may also be periodically replaced.

Figure 2:
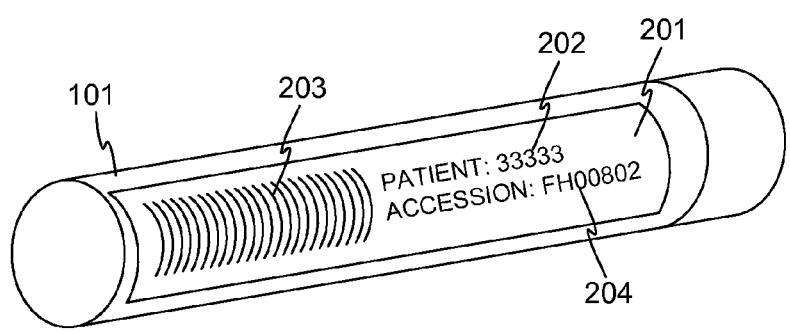
FIG. 2 shows a vial as may be used in the medical testing machine of FIG. 1, in more detail.

FIG. 2 shows a vial 101 in more detail. Each vial 101 is labeled with a machine-readable label 201 carrying information about the sample. Many different label formats are possible. Example label 201 includes a patient identifier 202, which may be shown in human-readable form as well as in machine readable form such as in barcode 203. Label 201 may also include an accession number 204. An accession number may be a numeric, alphabetic, alphanumeric, symbolic, or other identifier unique to a particular media sample. Accession number 204 may also be encoded into barcode 203.

Figure 3:
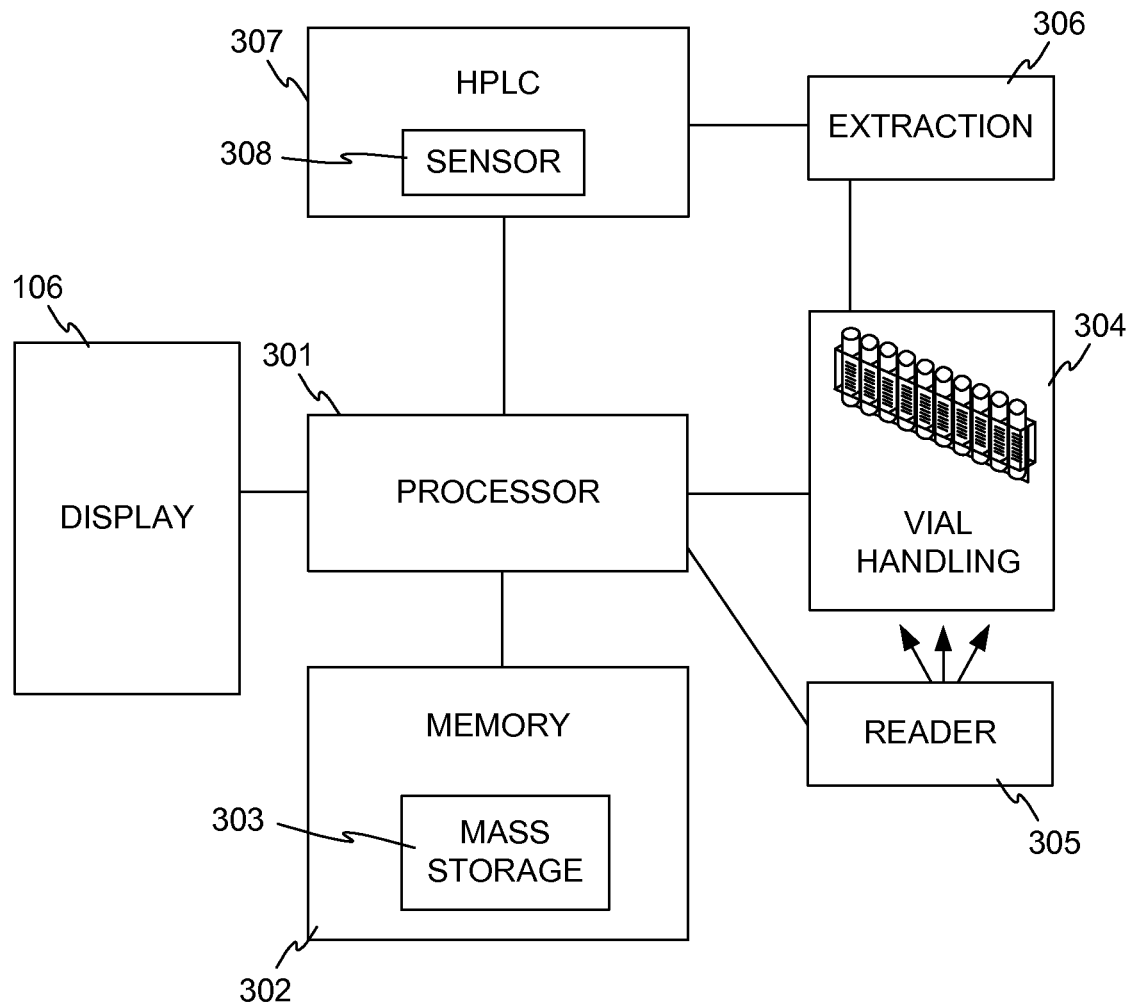
FIG. 3 shows a simplified block diagram of the architecture of the medical testing machine of FIG. 1, in accordance with embodiments of the invention.

FIG. 3 shows a simplified block diagram of the architecture of medical testing machine 100, in accordance with embodiments of the invention. A processor 301 generally controls the operation of medical testing machine 100. Processor 301 may be any suitable kind of microprocessor, microcontroller, digital signal processor, or other circuitry capable of performing the required functions. Memory 302 may include different kinds of memory, alone or in combination, and stores a variety of digital information. For example, memory 302 may include random access memory (RAM), read only memory (ROM), re-writable non-volatile memory such as flash memory, other kinds of memory, or any suitable combination thereof. In particular, memory 302 includes mass storage 303 for non-volatile storage of large quantities of information, for example the results of tests performed by medical testing machine 100. Mass storage 303 may include magnetic disk storage, optical disk storage, solid state memory, other kinds of storage, or any suitable combination thereof.

A portion of memory 302 preferably holds instructions that, when executed by processor 301, cause medical testing machine 100 to perform its intended functions.

Medical testing machine 100 includes a vial handling mechanism 304, for moving vials of patient samples through the system for testing. A vial reader 305 reads information from vials 101. For example, vial reader 305 may be a barcode reader that reads bar coded information such as patient and accession numbers 202 and 204 from a label such as label 201. In other embodiments, a different mechanism may be provided for obtaining information about a sample, for example a radio frequency identification (RFID) scanner, optical character recognition, or another suitable mechanism. In some embodiments, a user may enter information manually.

An extraction mechanism 306 automatically, under control of processor 301, extracts blood from each vial in turn for testing, and delivers the samples to high performance liquid chromatography (HPLC) system 307. In general, liquid chromatography involves introducing a small quantity of the sampled blood into the flow of a liquid medium, and passing the liquid medium through a stationary medium. Different components of the introduced blood will traverse the stationary medium at different speeds, due to their different interactions with the liquid and stationary media. The stationary medium is sometimes referred to as a "column". After a time, different components of the introduced blood sample will become separated within the column, and the separated components will arrive at the end of the column at different times. A sensor 308 near the end of the column watches for indications that the different components are passing. The indications may be differences in color, refractive index, spectral absorption characteristics, pH, or other characteristics. A brief overview of chromatography is given in co-pending U.S. patent application Ser. No. 13/675,022 filed Nov. 13, 2012 and titled "Chromatography Configuration Interface", the entire disclosure of which is hereby incorporated by reference herein.

The output of sensor 308 passes data to processor 301, which determines the result of the test. Results may be shown on display screen 106. Test results are stored in mass storage 303, in association with other information such as the information read from the vial labels. In particular, a particular test result may be stored in association with the accession number for the tested media, which may later be associated with patient information. Other kinds of information that are preferably included in the test information include the raw sensor output from the test, the time of the most recent calibration of medical testing machine 100 and the resulting calibration parameters, serial numbers or other identifying information about the consumable items used in the test, and any retest rules that were in place at the time of the test. Other kinds of information may also be stored. For example, a particular test may not produce a numerical result, because of a problem with the sample or an irregularity in the particular test. In this situation, the outcome of the test may be that there is no numerical result to report. For the purposes of this disclosure, the term "outcome" encompasses test outcomes with or without numerical results.

While mass storage 303 is depicted in FIG. 3 as being internal to medical testing machine 100, other arrangements are possible, and it is intended that the appended claims encompass other arrangements. For example, some or all of mass storage 303 may be external to medical testing machine 100 and connected to medical testing machine 100 by a cable or wireless interface. In some embodiments, mass storage 303 may be in a different location than medical testing machine 100 and connected to medical testing machine 100 through a computer network.

In order to ensure correct results and proper interpretation of those results, it is important that medical testing machine 100 be calibrated before its first use and periodically thereafter. Calibration typically involves presenting one or more calibration materials having known characteristics to medical testing machine 100. The calibration material may be actual test media or a synthesized material that mimics actual test media. The calibration material is prepared so as to produce a specific test result, called the assigned value of the calibration material. The calibration material is tested using the testing system, and it will be assumed that the raw output of a test on a particular calibration material corresponds to the assigned value of that calibration material.

One or more calibration parameters are determined that can be used to adjust the raw output to match the assigned value. The parameters are stored and applied to future tests of patient media samples.

Figure 4A:
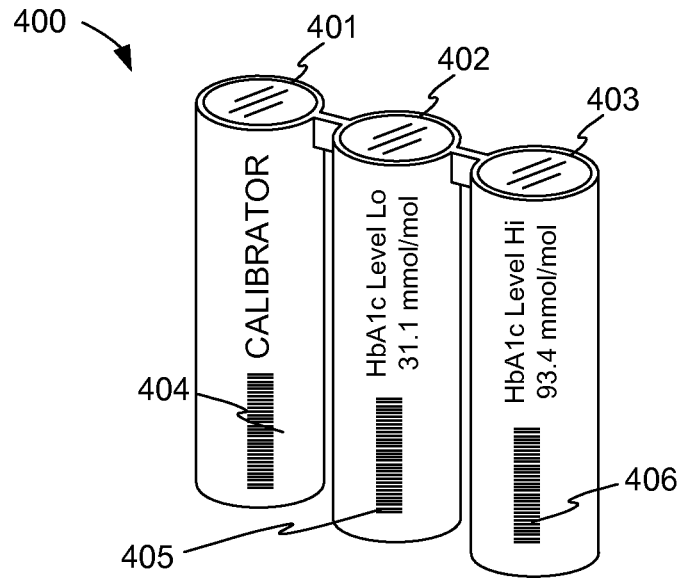
FIG. 4A illustrates a package of calibration materials according to one embodiment.

An example is helpful in explaining the process. FIG. 4A illustrates a package 400 of calibration materials according to an example embodiment. Although other configurations may be used, example package 400 is formed to conveniently be placed into a rack such as one of racks 102 and comprises three vials 401, 402, and 403, which are joined together. Vials 401-403 may be of the shape and size of standard blood collection vials, and are examples of containers that maintain separation between the calibration materials in package 400. Vial 401 may contain a conditioning fluid, while vials 402 and 403 contain two different calibration materials. Vial 402 contains a first material having a first assigned value for the HbA1c concentration (31.1 mmol/mol in this example), and vial 403 contains a second material having a second assigned value for the HbA1c concentration (93.4 mmol/mol in this example). Package 400 may be marked in such a way that medical testing machine 100 can automatically recognize it as a package of calibration materials. For example, a first barcode 404 may encode an indication that package 400 is a package of calibration materials, so that when reader 305 encounters barcode 404, processor 301 immediately recognizes that a calibration sequence is to be run, rather than testing a patient media sample. Other information may be encoded into barcode 404 as well, for example an expiration date of the calibration materials in package 400, a lot number, or other information.

Package 400 may be presented to a medical testing machine in any workable manner, for example by placing it in a rack in input location 103 of medical testing machine 100, or in STAT input 105.

In some embodiments, additional barcodes such as barcodes 405 and 406 may provide other information to medical testing machine 100. For example, barcode 405 may encode the assigned value for the material in vial 402 (31.1 mmol/mol in this example), and barcode 406 may encode the assigned value from the material in vial 403 (93.4 mmol/mol in this example). These values may also be called setpoints, and may be determined at the time the calibration materials are manufactured.

Figure 4B:
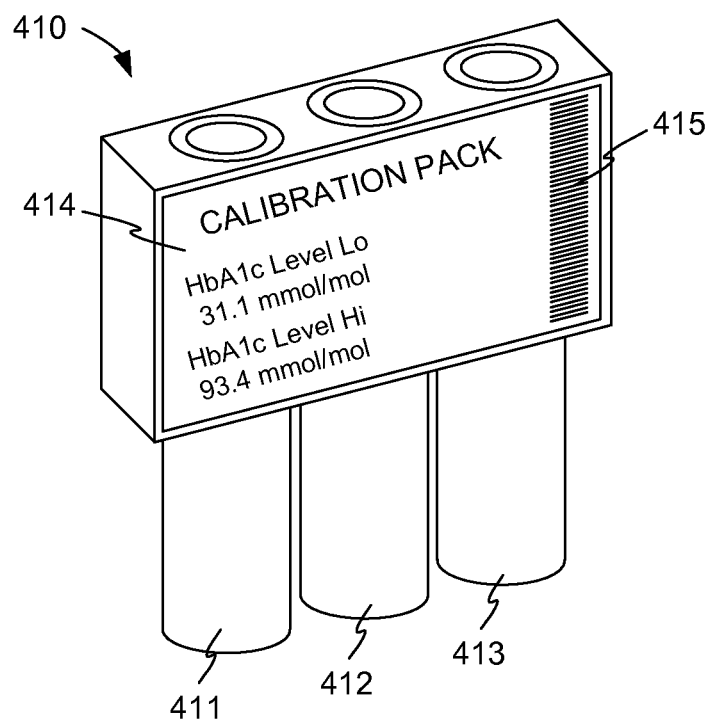
FIG. 4B illustrates a package of calibration materials according to another embodiment.

FIG. 4B illustrates a package 410 of calibration materials according to another example embodiment. Example package 410 includes vials 411, 412, and 413 for holding a conditioning fluid and calibration materials. A label 414 identifies package 410 as a calibration package, and includes a barcode 415 that encodes various information about package 410. For example, barcode 415 may encode the assigned values of the calibration materials in vials 412 and 413, an expiration date, a lot number, or other kinds of information. Other calibration configurations are also possible.

In some embodiments, medical testing machine 100 may present a user interface screen upon recognition that a calibration sequence is to be run. FIG. 5 illustrates an example user interface screen 500 that may be presented on a display such as display 106. A user of medical testing machine 100 can use user interface screen 500 to instruct medical testing machine to proceed with the calibration sequence, to cancel the calibration, or to take other actions.

Extraction mechanism 306 may be capable of, under control of processor 301, performing any mixing or other necessary processing needed in the calibration sequence. For example, extraction mechanism 306 may extract conditioning fluid from vial 401 to prepare the column to run tests. One or more of consumables 107 may be dispensed into either or both of vials 402 and 403, in order to condition the materials in those vials for the calibration sequence.

Medical testing machine then extracts samples from vials 402 and 403, performs its test on them, and stores the results. Because two different materials having different assigned values are tested in this example, this is a two-point calibration. It will be recognized that other embodiments may use a single calibration material, or more than two calibration materials.

For the purposes of this example, we assume that the test on the material in vial 402 results in a reading of 30.5 mmol/mol, and the test on the material in vial 403 results in a reading of 94.9 mmol/mol. These results are summarized in Table 1 below.

TABLE 1

| Assigned Value | Actual Reading |
| --- | --- |
| 31.1 | 30.5 |
| 93.4 | 94.9 |

Assuming that the discrepancies between the assigned values and the actual readings are due to miscalibration of the medical testing machine, it appears that medical testing machine 100 provides results that are too low for materials with low HbA1c concentrations, and results that are too high for materials with high HbA1c concentrations.

Medical testing machine 100, using processor 301, can ascertain calibration parameters to be applied to future tests to correct the results of future tests. For a two-point calibration, two parameters can be determined based on a linear transformation of the actual readings to the assigned values. It is straightforward to determine for the example readings in Table 1 that Assigned Value=0.9674*Actual Reading+1.5946

In this example, the two calibration parameters are the slope (0.9674) and intercept (1.5946) of a linear conversion of the actual readings to the assigned values. Assuming that this linear transformation will improve the accuracy of readings at other concentration levels, the slope and intercept are stored and the linear transformation is applied to the results of future tests. For example, if in a future test of media sampled from a patient medical testing machine 100 initially obtains a reading of 77.4 mmol/mol, that reading would be adjusted before reporting according to Reported result=0.9674*77.4+1.5946=76.5 mmol/mol.

The slope and intercept determined in an actual embodiment will depend on the particular testing machine used, the kind of test being performed, and other variables.

In some embodiments, the internal measurements units used by the testing machine may differ from the units in which test results are presented. For example, in the case of HPLC testing for HbA1c levels, medical testing machine 100 may compute the area of a particular peak in the chromatogram to measure the HbA1c level, but report the test result in mmol/mol. This conversion may be reflected in the calibration.

Example data for performing a calibration including a unit conversion are shown in Table 2 below. In this example, the unit used internally by the medical testing machine for HbA1c concentration is the area of the chromatogram attributed to the HbA1c peak, in arbitrary units.

TABLE 2

| Assigned Value (mmol/mol) | Actual Reading (arbitrary area units) |
|---|---|
| 31.1 | 3.282 |
| 93.4 | 7.679 |

It is straightforward to determine for the example readings in Table 2 that

Assigned Value(mmol/mol)=14.169*Actual Reading (arbitrary units)−15.405

Thus, a future test that results in an area reading of 7.4 arbitrary units would be reported as Reported result=14.169*7.4−15.405=89.4 mmol/mol.

Other unit conversions may be implemented in this manner.

In other embodiments, more or fewer calibration points may be used. In a one-point calibration, the single calibration parameter may be a simple scaling factor or offset applied to measured results before reporting. In a three-point calibration, the transformation between the initial and reported readings can be more complex, for example a quadratic formula.

In some embodiments, one or more of the calibration materials are stored in a lyophilized form. For example, either or both of the materials in vials 402 and 403 may be in lyophilized form. In this case, the material is reconstituted before testing is done by adding a liquid to the material. The liquid used for reconstitution may be provided in the calibration package, for example in vial 401, or a liquid already existing in the medical testing machine may be used. For example, in the case of medical testing machine 100 that performs chromatography, the washing solution used in the chromatography may also be used to reconstitute lyophilized calibration materials.

In reconstituting the lyophilized material, liquid may be added to the lyophilized material and the mixture agitated. In some embodiments, the agitation is accomplished by aspirating some or all of the mixture from the vial being agitated using extraction mechanism 306 and re-injecting the aspirated mixture into the vial. The aspiration and re-injection may be performed as many times as is necessary to ensure thorough mixing.

In some cases, a medical testing machine according to embodiments may recognize that the calibration failed, and may automatically repeat the calibration. For example, after ascertaining the calibration parameters, processor 301 may compare them with predetermined condition and repeat the calibration if the parameters do not meet the predetermined condition. In the example above, the slope parameter should always be a value greater than zero. If the result of a calibration is that the slope parameter is negative, the calibration is obviously faulty. In this case, the predetermined condition is that the slope parameter must be positive.

In other embodiments, a calibration may be repeated if a parameter falls outside of an expected range. For example, a calibration may be repeated if the slope differs by more than a predetermined percentage from its expected value, or if the intercept differs by more than a predetermined amount from its expected value. The predetermined amounts will depend on the particular test being performed, the number and kind of calibration parameters, the measurement units used for the actual and expected test results, and other factors. In some embodiments, a test may be repeated if the slope differs from its expected value by more than 1 percent, 2 percent, 5 percent, 10 percent, 25 percent, or another suitable amount. If a repeat calibration still does not produce calibration parameters that are within the expected ranges, the machine may signal that it is in need of maintenance.

Figure 6:
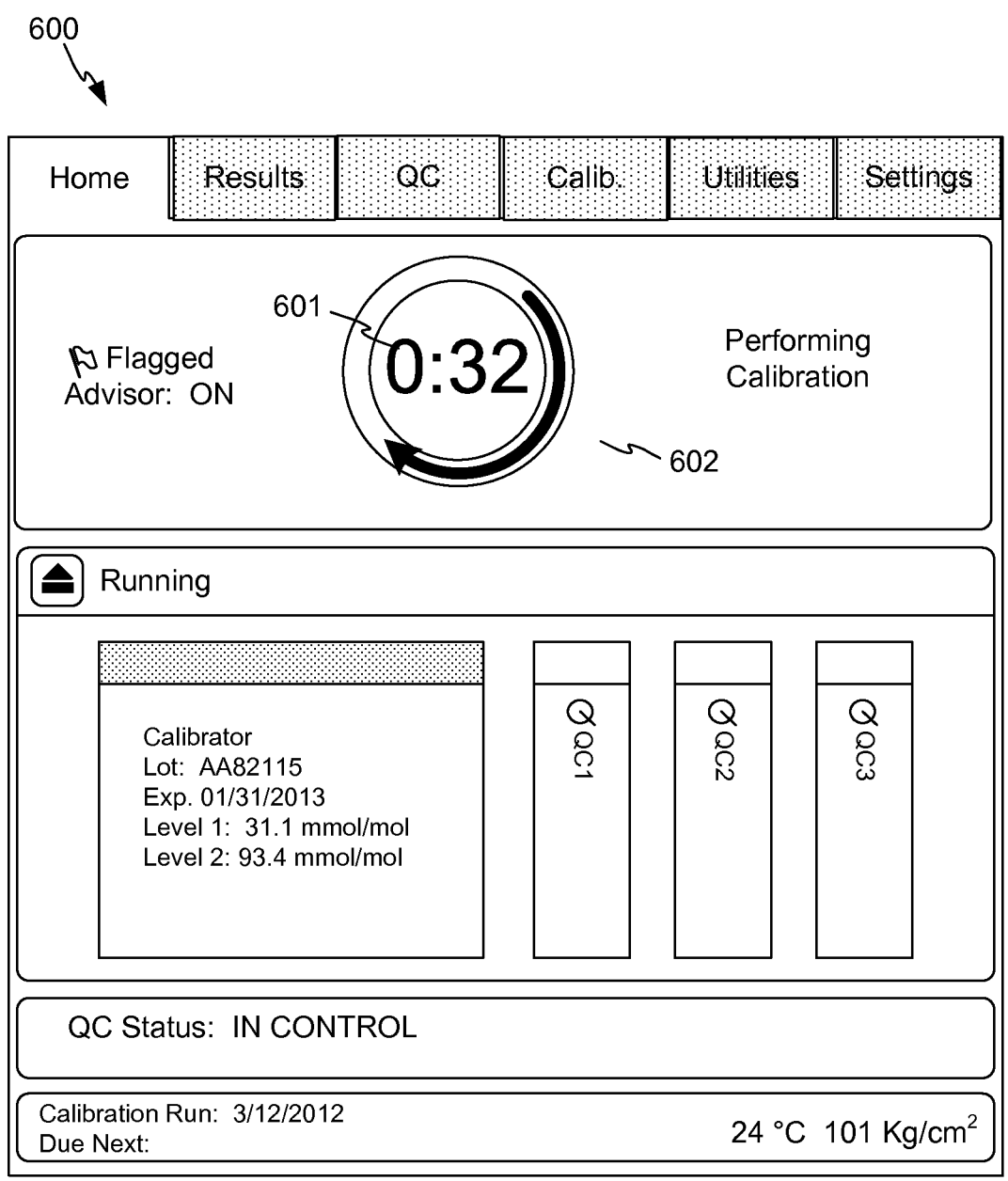
FIG. 6 shows an example user interface screen for providing user feedback about the progress of a calibration sequence.

In some embodiments, a medical testing machine provides user feedback about the progress of a calibration. FIG. 6 shows an example user interface screen 600 for this purpose. In example user interface screen 600, an animated counter 601 counts down the time remaining in the calibration sequence. An arrow 602 or shaded feature may rotate around counter 601 to indicate that testing is progressing. For example, arrow 602 may rotate about once per second, or at another suitable speed. Other areas of user interface screen 600 may visually indicate the progress of the calibration. For example, activities may be highlighted in the display. The highlighting may be accomplished by the use of color, animation, or other suitable graphical techniques.

Preferably, a testing machine in accordance with embodiments stores information about the calibration sequence for later retrieval and examination. The stored information may include the chromatogram obtained for each calibration material, the result measured for each calibration material, the calibration parameters such as a slope and intercept ascertained in the calibration, or other information.

Figure 7:
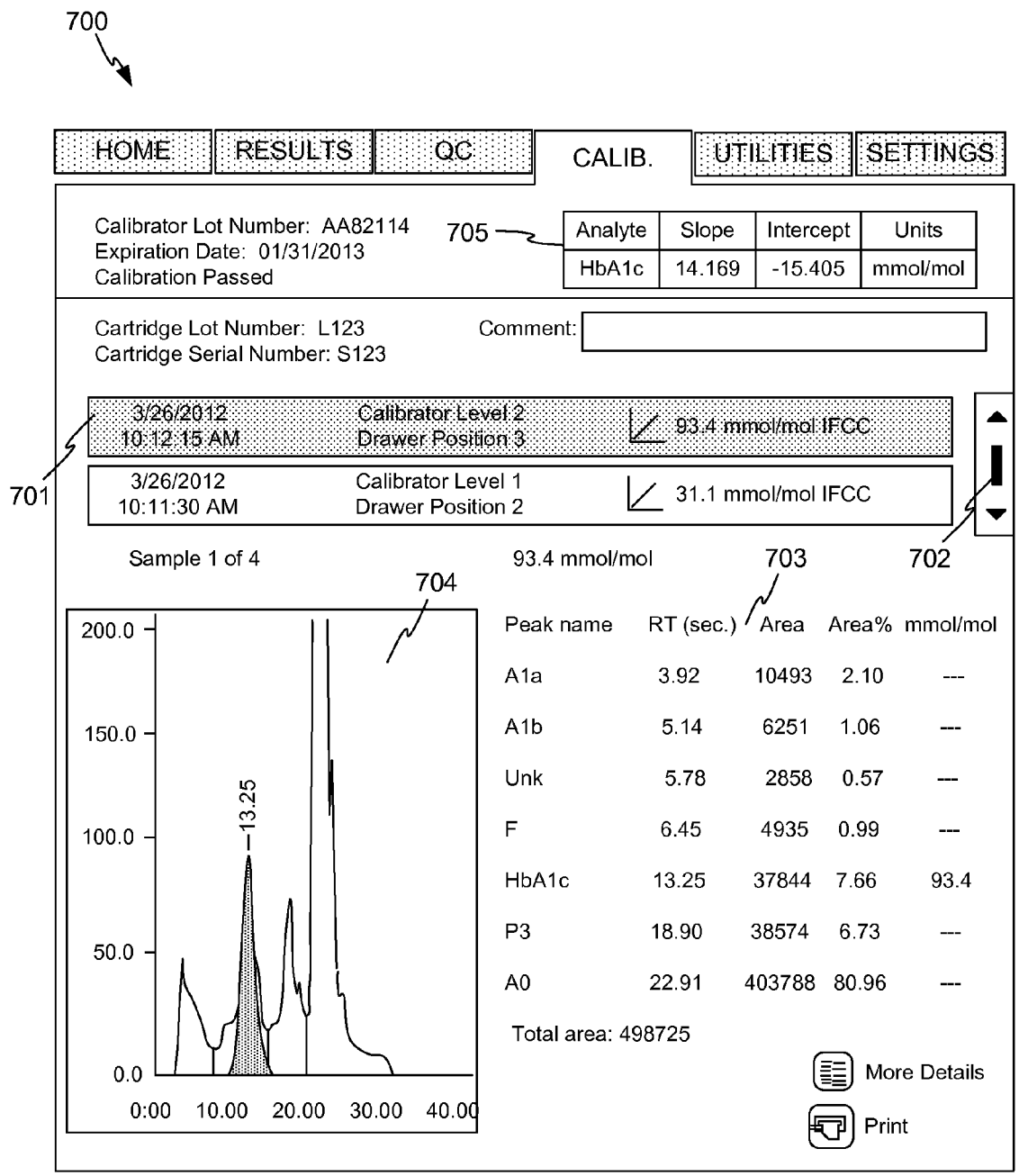
FIG. 7 illustrates an example user interface screen for recalling stored information relating to a calibration sequence.

FIG. 7 illustrates an example user interface screen 700 for recalling stored information relating to a calibration sequence. In user interface screen 700, a user may highlight the test of a particular calibration material, for example by touching screen 106. In FIG. 7, a particular calibrator result 701 has been highlighted. Another control 702 may allow selection of particular calibrator results associated with the calibration. In example screen, both tabular data 703 and the chromatogram 704 for the highlighted calibrator sample are displayed. The calibration parameters are also displayed 705.

While embodiments of the invention have been described above in the context of a machine that tests blood for levels of HbAlc hemoglobin using HPLC, it is to be understood that the claims are not so limited, and that the principles of the invention may be embodied in other kinds of testing machines that perform different tests on other fluids, tissue, or other patient media. It is to be understood that all workable combinations of the features and capabilities described herein are also considered to be disclosed. For example, medical testing machine embodying the invention may include any one, any combination, or all of the compatible features and capabilities described above.

The invention has now been described in detail for the purposes of clarity and understanding. However, it will be appreciated that certain changes and modifications may be practiced within the scope of the appended claims.

What is claimed is:

1. A method of performing a calibration in a medical testing machine, the method comprising:
   automatically detecting that a package of calibration material has been inserted into the medical testing machine;
   performing, by the medical testing machine, a calibration sequence using the calibration material to ascertain a calibration parameter for the medical testing machine; and
   storing the calibration parameter in electronic storage for use in later tests performed by the medical testing machine;
   wherein the calibration material is provided in a lyophilized state, the method further comprising controlling the medical testing machine to automatically reconstitute the lyophilized material before performing the calibration sequence.

2. The method of claim 1, further comprising reading a calibration setpoint from the package of calibration material.

3. The method of claim 1, wherein the medical testing machine performs liquid chromatography that uses a washing solution, and wherein the washing solution is also used to reconstitute the lyophilized material.

4. The method of claim 1, further comprising agitating the reconstituted material by aspirating at least some of the reconstituted material from its vial and re-injecting the aspirated reconstituted material into its vial.

5. The method of claim 1, wherein the medical testing machine performs high performance liquid chromatography.

6. The method of claim 1, wherein the medical testing machine performs a test that measures a level of HbAlc hemoglobin in blood.

7. The method of claim 1, further comprising:
   comparing the calibration parameter with a predetermined condition; and
   automatically re-running the calibration if the calibration parameter does not meet the predetermined condition.

8. The method of claim 1, further comprising:
   comparing the calibration parameter with a predetermined condition; and
   automatically re-running the calibration if the calibration parameter meets the predetermined condition.

9. The method of claim 1, wherein the calibration is a two-point calibration, and wherein two calibration parameters are ascertained.

10. The method of claim 9 wherein the calibration parameters include a slope and an intercept.

11. A medical testing machine, comprising:
    a testing system for performing a medical test on media sampled from patients;
    a media handling mechanism;
    a processor; and
    a memory, the memory holding instructions that when executed by the processor cause the medical testing machine to:
      automatically recognize that a package of calibration material has been inserted into the medical testing machine, wherein the package holds two materials, at least one of which is a calibration material in a lyophilized state, and the package includes a respective container for each of the materials, the containers maintaining separation between the materials before use of the calibration package, and wherein the package is received from outside the medical testing machine;
      automatically reconstitute the lyophilized calibration material;
      after the lyophilized calibration material is reconstituted, perform a calibration sequence using the calibration material to ascertain a calibration parameter for the medical testing machine; and
      store the calibration parameter in the memory for use in later tests performed by the medical testing machine.

12. The medical testing machine of claim 11, further comprising a STAT input, wherein the medical testing machine automatically recognizes that the package of calibration material has been inserted into the STAT input.

13. The medical testing machine of claim 11, wherein the medical testing machine performs high performance liquid chromatography.

14. The medical testing machine of claim 11, wherein the medical testing machine performs a test that measures a level of HbAlc hemoglobin in blood.

15. The medical testing machine of claim 11, further comprising a display, and wherein the instructions, when executed by the processor, further cause the medical testing machine to present a user interface screen on the display indicating the progress of the calibration sequence.

16. The medical testing machine of claim 15, wherein the display is a touchscreen display.

17. The method of claim 1, wherein the package holds two materials, at least one of which is calibration material, and the package includes a respective container for each of the materials, the containers maintaining separation between the materials before use of the calibration package, and wherein the package is received from outside the medical testing machine.

* * * * *